United States Patent
Yang et al.

(10) Patent No.: US 10,335,615 B2
(45) Date of Patent: Jul. 2, 2019

(54) ORAL CARE COMPOSITIONS AND METHODS OF USE

(71) Applicant: Colgate-Palmolive Company, New York, NY (US)

(72) Inventors: Ying Yang, Monmouth Junction, NJ (US); Dandan Chen, Bridgewater, NJ (US); Robert D'Ambrogio, Princeton, NJ (US); Paul Thomson, Piscatatway, NJ (US); Harsh Mahendra Trivedi, Hillsborough, NJ (US); Michael Prencipe, West Windsor, NJ (US); James Masters, Ringoes, NJ (US); Stanislav Jaracz, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 3 days.

(21) Appl. No.: 15/629,190

(22) Filed: Jun. 21, 2017

(65) Prior Publication Data

US 2017/0368376 A1    Dec. 28, 2017

Related U.S. Application Data

(60) Provisional application No. 62/354,279, filed on Jun. 24, 2016.

(51) Int. Cl.

| | |
|---|---|
| *A61K 8/21* | (2006.01) |
| *A61K 8/22* | (2006.01) |
| *A61K 8/27* | (2006.01) |
| *A61K 8/34* | (2006.01) |
| *A61K 8/35* | (2006.01) |
| *A61K 8/97* | (2017.01) |
| *A61K 45/06* | (2006.01) |
| *A61K 8/365* | (2006.01) |
| *A61Q 11/00* | (2006.01) |
| *A61Q 17/00* | (2006.01) |
| *A61K 36/9068* | (2006.01) |

(52) U.S. Cl.
CPC ............ *A61Q 11/00* (2013.01); *A61K 8/21* (2013.01); *A61K 8/22* (2013.01); *A61K 8/27* (2013.01); *A61K 8/34* (2013.01); *A61K 8/347* (2013.01); *A61K 8/35* (2013.01); *A61K 8/365* (2013.01); *A61K 8/97* (2013.01); *A61K 36/9068* (2013.01); *A61K 45/06* (2013.01); *A61Q 17/005* (2013.01)

(58) Field of Classification Search
CPC .............. A61K 8/19; A61K 8/22; A61K 8/34
USPC .............................. 424/48, 49, 58; 426/532
See application file for complete search history.

(56) References Cited

U.S. PATENT DOCUMENTS

| | | | |
|---|---|---|---|
| 2,876,166 A | | 3/1959 | Nebergall |
| 4,961,924 A | | 10/1990 | Suhonen |
| 5,188,820 A | | 2/1993 | Cummins et al. |
| 6,685,920 B2 | | 2/2004 | Baig et al. |
| 6,696,045 B2 | | 2/2004 | Yue et al. |
| 8,906,347 B2 | | 12/2014 | Strand et al. |
| 8,906,349 B2 | | 12/2014 | Schaeffer-Korbylo et al. |
| 8,962,037 B2 | | 2/2015 | Haught et al. |
| 9,655,838 B2 | | 5/2017 | Prencipe et al. |
| 2010/0278991 A1 | * | 11/2010 | Haught ............... A61K 8/19 426/532 |
| 2012/0207686 A1 | | 8/2012 | Fisher et al. |
| 2013/0209375 A1 | | 8/2013 | Moya Argilagos et al. |
| 2014/0377191 A1 | * | 12/2014 | Gadkari ............... A61K 8/19 424/49 |
| 2015/0335539 A1 | | 11/2015 | Prencipe et al. |
| 2016/0303010 A1 | | 10/2016 | Prencipe et al. |
| 2017/0246092 A1 | | 8/2017 | Prencipe et al. |

FOREIGN PATENT DOCUMENTS

| | | | |
|---|---|---|---|
| JP | S63-33326 A | 2/1998 | |
| WO | WO 2009/130319 | 10/2009 | |
| WO | WO 2011/053291 | 5/2011 | |
| WO | WO2014100928 | * 7/2014 | ............ A61Q 11/00 |

OTHER PUBLICATIONS

International Search Report and Written Opinion in International Application No. PCT/US2017/038508, dated Sep. 1, 2017.

* cited by examiner

*Primary Examiner* — Walter E Webb

(57) ABSTRACT

This invention relates to oral care compositions comprising zingerone, bisabolol, a stannous ion source, zinc oxide, and zinc citrate, as well as to methods of using and of making these compositions.

17 Claims, No Drawings

ORAL CARE COMPOSITIONS AND METHODS OF USE

CROSS REFERENCE TO RELATED APPLICATIONS

This application claims priority benefit of U.S. Provisional Application No. 62/354,279, filed on Jun. 24, 2016, the contents of which are incorporated herein by reference.

This invention relates to oral care compositions comprising zingerone, bisabolol, a stannous ion source, zinc oxide, and zinc citrate, as well as to methods of using and of making these compositions.

BACKGROUND

Sodium fluoride and stannous fluoride are known as useful fluoride sources for dentifrices. Stannous fluoride possesses an advantage over some other ionic fluorides, including sodium fluoride, in that it is antimicrobial—it kills bacteria in the mouth by interfering with the bacterial metabolic processes. However there are challenges with retained deposition of stannous.

There is a need for improved antibacterial toothpaste formulations that do not suffer from the drawbacks of conventional compositions, and that provide additional antimicrobial benefits.

BRIEF SUMMARY

It has been surprisingly found that the inclusion of bisabolol in an oral care composition comprising a stannous ion source, zinc oxide and/or zinc citrate, and zingerone, selected at certain concentrations and amounts, unexpectedly and synergistically increases the deposition of stannous (i.e., stannous ions) on soft gingival tissue, thus increasing the antibacterial effect of the oral care composition, in the oral cavity of a user. The current formulations offer the advantage of robust microbial protection without significantly interfering with the stability of the oral care composition.

In one aspect the present disclosure provides an oral care composition
(Composition 1.0) comprising:
 a. bisabolol;
 b. zinc oxide;
 c. zinc citrate;
 d. zingerone; and
 e. a stannous ion source.

For example, the invention contemplates any of the following compositions (unless otherwise indicated, values are given as percentage of the overall weight of the composition):

1.1 Composition 1.0 wherein the bisabolol is present in an amount of from 0.01% to 1% (e.g., 0.05% to 0.5%; e.g., 0.05% to 0.35%; e.g., 0.1%, 0.2%, or 0.3%).

1.2 Any of the preceding compositions, wherein the zingerone is present in an amount of from 0.01% to 1% (e.g., 0.05% to 0.5%; e.g., 0.05% to 0.35%; e.g., 0.1%, 0.2%, or 0.3%).

1.3 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.4 Any of the preceding compositions, wherein the zinc citrate is in an amount of from 0.25 to 1.0 wt % (e.g., 0.5 wt. %) and zinc oxide may be present in an amount of from 0.75 to 1.25 wt % (e.g., 1.0 wt. %) based on the weight of the oral care composition.

1.5 Any of the preceding compositions wherein the zinc citrate is about 0.5 wt %.

1.6 Any of the preceding compositions wherein the zinc oxide is about 1.0 wt %.

1.7 Any of the preceding compositions where the zinc citrate is about 0.5 wt % and the zinc oxide is about 1.0 wt %.

1.8 Any of the preceding compositions wherein the stannous ion source is stannous fluoride.

1.9 Any of the preceding compositions wherein the stannous ion source is a fluoride salt present in an amount of 0.1 wt. % to 2 wt. %/0, e.g. 0.1 wt %-0.6 wt. %, e.g., stannous fluoride in an amount of about 0.4-0.5 wt. % of the total composition weight.

1.10 Any of the preceding compositions wherein the fluoride source is stannous fluoride in an amount sufficient to provide fluoride ion in an amount of from 50 to 25,000 ppm (e.g., 750-2000 ppm, e.g., 1000-1500 ppm, e.g., about 1100 ppm).

1.11 Any of the preceding compositions further comprising an abrasive or particulate (e.g., silica).

1.12 Any of the preceding compositions wherein the silica is synthetic amorphous precipitated abrasive silica. (e.g., 1%-25% by wt.) (e.g., 8%-25% by wt.) (e.g., 10%-15% by wt.).

1.13 Any of the preceding composition further comprising a high cleaning silica. (e.g., 1%-15% by wt.) (e.g., 5%-10% by wt.) (e.g., about 7% by wt.).

1.14 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshphate, monosodium phosphate, pentapotassium triphosphate and mixtures of any of two or more of these, e.g., in an amount of 1-20%, e.g., 2-8%, e.g., 2-5%, by weight of the composition.

1.15 Any of the preceding compositions comprising a polyphosphate.

1.16 The composition of 1.15, wherein the polyphosphate is sodium tripolyphosphate.

1.17 The composition of 1.16, wherein the sodium tripolyphosphate is from 1-5 wt % (e.g., about 3 wt %).

1.18 Any of the preceding compositions further comprising citric acid and tribasic citrate ion, for example citric acid in an amount of from 0.1-3 wt. %, e.g., 0.1-1 wt. %, e.g., 0.4-0.8 wt. %, e.g. about 0.6 wt. %; and citrate ion, for example trisodium citrate dihydrate, in an amount of from 0.1-5 wt. %, e.g., 2-4 wt. %, e.g., about 3 wt. %.

1.19 Any of the preceding compositions, wherein the composition comprises carboxymethyl cellulose (e.g., from 0.1 wt. %-1.5 wt. %, e.g., 0.1 wt. %-0.5 wt. %).

1.20 Any of the preceding compositions further comprising an anionic surfactant, wherein the anionic surfactant is in an amount of from 0.5-5%, e.g., 1-2%, e.g., sodium lauryl sulfate.

1.21 Any of the preceding compositions further comprising an amphoteric surfactant, wherein the amphoteric surfactant is in an amount of from 0.5-5%, e.g., 0.5-1.5%, e.g., cocamidopropyl betaine.

1.22 Any of the preceding compositions further comprising glycerin, wherein the glycerin is in a total amount of 20-60% (e.g., about 40%).
1.23 Any of the preceding compositions further comprising a polymer, e.g., a PVM/MA copolymer, in an amount of from 0.1-5%, e.g., 0.2-2%, e.g., 0.3-1%.
1.24 Any of the preceding compositions further comprising microcrystalline cellulose/sodium carboxymethylcellulose, e.g., in an amount of from 0.1-5%, e.g., 0.5-2%, e.g. 1%.
1.25 Any of the preceding compositions further comprising one or both of:
   a. Polyethylene glycol in an amount of from 1-6%; and
   b. Propylene glycol in an amount of from 1-6%.
1.26 Any of the preceding compositions further comprising polyvinylpyrrolidone (PVP) in an amount of from 0.5-3 wt. %, e.g. about 1.25 wt. %.
1.27 Any of the preceding compositions comprising from 5%-40%, e.g., 5%-25%, e.g., 5%-15%, e.g., about 8-10% water by weight.
1.28 Any of the preceding compositions comprising flavoring, fragrance and/or coloring.
1.29 The composition of 1.28, wherein the flavoring agent is sodium saccharin, sucralose, or a mixture thereof.
1.30 Any of the preceding compositions, wherein the composition comprises one or more thickening agents selected from the group consisting of carboxyvinyl polymers, carrageenan, hydroxyethyl cellulose and water soluble salts of cellulose ethers (e.g., sodium carboxymethyl cellulose and sodium carboxymethyl hydroxyethyl cellulose).
1.31 Any of the preceding compositions comprising an additional antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
1.32 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.
1.33 Any of the preceding compositions further comprising a basic amino acid.
1.34 Composition 1.35 wherein the basic amino acid has the L-configuration (e.g., L-arginine).
1.35 Any of the preceding compositions 1.33-1.34 wherein the basic amino acid is arginine or lysine is in free form.
1.36 Any of the preceding compositions 1.33-1.35 wherein the basic amino acid is provided in the form of a di- or tri-peptide comprising arginine or lysine, or salts thereof.
1.37 Composition 1.38 wherein the basic amino acid is selected from:
   a. a tripeptide comprising one lysine and two arginines;
   b. a tripeptide comprising one arginine and two lysines; and
   c. a tetrapeptide comprising at least one arginine, at least one lysine, and at least one linker amino acid that directly links or indirectly links (i.e., thorough another amino acid) the arginine and the lysine; e.g., where the linker amino acid is glycine.
1.38 Any of the preceding compositions 1.33-1.37 wherein the basic amino acid is arginine or lysine, and wherein the arginine or lysine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.
1.39 Any of the preceding compositions 1.33-1.38 wherein the amino acid is arginine from 0.1 wt. %-6.0 wt. %. (e.g., about 1.5 wt %).
1.40 Any of the preceding compositions 1.33-1.39 wherein the amino acid is arginine from about 1.5 wt. %.
1.41 Any of the preceding compositions 1.33-1.40 wherein the amino acid is arginine from 4.5 wt. %-8.5 wt. % (e.g., 5.0%).
1.42 Any of the preceding compositions 1.33-1.41 wherein the amino acid is arginine from about 5.0 wt. %.
1.43 Any of the preceding compositions 1.33-1.41 wherein the amino acid is arginine from 3.5 wt. %-9 wt. %.
1.44 Any of the preceding compositions 1.33-1.41 wherein the amino acid is arginine from about 8.0 wt. %.
1.45 Any of the preceding compositions 1.33-1.44 wherein the amino acid is L-arginine.
1.46 Any of the preceding compositions 1.33-1.45 wherein the amino acid is free form arginine.
1.47 Any of the preceding compositions 1.33-1.46 wherein the basic amino acid is lysine (e.g., 2% wt., 3% wt., 4% wt., 5% wt., 6% wt.), (e.g., 4% wt.).
1.48 Any of the preceding compositions 1.33-1.47 wherein the amino acid is lysine from 1.0 wt. %-6.0 wt. %.
1.49 Any of the preceding compositions 1.33-1.48 wherein the amino acid is lysine from about 1.5 wt. %.
1.50 Any of the preceding compositions 1.33-1.49—wherein the amino acid is lysine from about 4.0 wt. %.
1.51 Any of the preceding compositions 1.33-1.50 wherein the amino acid is L-lysine.
1.52 Any of the preceding compositions 1.33-1.51 wherein the amino acid is free form lysine.
1.53 Any of the preceding compositions 1.33-1.52 wherein the amino acid is arginine or lysine in partially or wholly in salt form.
1.54 Composition 1.33 wherein the amino acid is arginine phosphate.
1.55 Composition 1.33 wherein the amino acid is arginine hydrochloride.
1.56 Composition 1.33 wherein the amino acid is arginine bicarbonate.

1.57 Composition 1.33 wherein the amino acid is lysine phosphate.
1.58 Composition 1.33 wherein the amino acid is lysine hydrochloride.
1.59 Composition 1.33 wherein the amino acid is lysine bicarbonate.
1.60 Any of the preceding compositions 1.33-1.59 wherein the amino acid is arginine or lysine ionized by neutralization with an acid or a salt of an acid.
1.61 Any of the preceding composition wherein the silica abrasives are silica gels or precipitated amorphous silicas, e.g. silicas having an average particle size ranging from 2.5 microns to 12 microns.
1.62 Any of the preceding compositions further comprising a small particle silica having a median particle size (d50) of 1-5 microns (e.g., 3-4 microns) (e.g., about 5 wt. % Sorbosil AC43 from PQ, Warrington, United Kingdom).
1.63 Any of the preceding compositions wherein 20-30 wt % of the total silica in the composition is small particle silica (e.g., having a median particle size (d50) of 3-4 microns) and wherein the small particle silica is about 5 wt. % of the oral care composition.
1.64 Any of the preceding compositions comprising silica wherein the silica is used as a thickening agent, e.g., particle silica.
1.65 Any of the preceding compositions further comprising a nonionic surfactant, wherein the nonionic surfactant is in an amount of from 0.5-5%, e.g., 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof.
1.66 Any of the preceding compositions comprising a whitening agent.
1.67 Any of the preceding compositions comprising a whitening agent selected from the group consisting of stannous peroxides, metal chlorites, perborates, percarbonates, peroxyacids, hypochlorites, and combinations thereof.
1.68 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.69 Any of the preceding compositions further comprising an agent that interferes with or prevents bacterial attachment, e.g., ELA or chitosan.
1.70 Any of the preceding compositions further comprising an additional ingredient selected from: benzyl alcohol, Methylisothiazolinone ("MIT"), Sodium bicarbonate, sodium methyl cocoyl taurate (tauranol), lauryl alcohol, and polyphosphate.
1.71 Any of the preceding compositions comprising:
   a. about 0.1-0.3% bisabolol;
   b. about 0.1-0.3% zingerone;
   c. about 1.0% zinc oxide;
   d. about 0.5% zinc citrate; and
   e. about 0.4%-0.5% stannous fluoride.
1.72 Any of the preceding compositions comprising:
   a. about 0.1-0.3% bisabolol;
   b. about 0.1-0.3% zingerone;
   c. about 1.0% zinc oxide;
   d. about 0.5% zinc citrate;
   e. about 0.4%-0.5% stannous fluoride; and
   f. about 12% abrasive silica.
1.73 Composition 1.72 further comprising about 70% high cleaning silica.
1.74 Any of the preceding Compositions 1.0-1.73, further comprising sodium phosphate in an amount of from 0.5 wt %-5 wt %, e.g., 0.5 wt. %-2 wt. %, e.g., about 1 wt. %.
1.75 Any of the preceding compositions effective upon application to the oral cavity, e.g., by rinsing, optionally in conjunction with brushing, to (i) reduce or inhibit formation of dental caries (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.
1.76 Any of the preceding oral compositions, wherein the oral composition may be any of the following oral compositions selected from the group consisting of a toothpaste or a dentifrice, a mouthwash or a mouth rinse, a topical oral gel, a chewing gum, and a denture cleanser.
1.77 A composition obtained or obtainable by combining the ingredients as set forth in any of the preceding compositions.

A composition obtained or obtainable by combining the ingredients as set forth in any of the preceding compositions.

A composition for use as set forth in any of the preceding compositions.

In a further embodiment, the present disclosure provides a method for increasing the efficacy of deposition of stannous ions on tissue, hard (e.g., teeth) and soft (e.g., gingival tissue, tongue), of a composition comprising zinc oxide, zinc citrate, zingerone, and a source of stannous ions, e.g., stannous fluoride, the method comprising combining the aforementioned ingredients with bisabolol.

In a further embodiment, the present disclosure provides a method for depositing stannous ions on gingival tissue, comprising contacting said tissue with a composition according to any of Compositions 1.0-1.79.

In another embodiment, the invention encompasses a method to improve oral health comprising applying an effective amount of the oral composition of any of the embodiments set forth above to the oral cavity of a subject in need thereof, e.g., a method to
   i. reduce or inhibit formation of dental caries,
   ii. reduce, repair or inhibit early enamel lesions, e.g., as detected by quantitative light-induced fluorescence (QLF) or electrical caries measurement (ECM),
   iii. reduce or inhibit demineralization and promote remineralization of the teeth, iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial bio film formation in the oral cavity,
x. raise and/or maintain plaque pH at levels of at least pH 5.5 following sugar challenge,
xi. reduce plaque accumulation,
xii. treat dry mouth,
xiii. enhance systemic health, including cardiovascular health, e.g., by reducing potential for systemic infection via the oral tissues,
xiv. Whiten teeth,
xv. reduce erosion of the teeth,
xvi. immunize (or protect) the teeth against cariogenic bacteria and their effects, and/or
xvii. clean the teeth and oral cavity.

The invention further comprises the use of sodium bicarbonate, sodium methyl cocoyl taurate (tauranol), MIT, and benzyl alcohol and combinations thereof in the manufacture of a composition as disclosed herein, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

Zingerone

Zingerone (4-(3-methoxy-4-hydroxyphenyl)-butan-2-one, also known as vanillylacetone), has the formula:

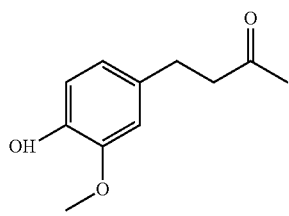

Zingerone is a key component of the pungency of ginger. Zingerone is a member of both the methoxyphenol family and its related derivatives, which have a basic phenolic ring with a methoxy group attached to benzene ring, and the phenolic alkanone group, which is characterized by having an alkanone group attached to the phenolic ring. Zingerone has varied pharmacological properties that include antioxidant, anti-inflammatory, anticancer, lipolytic, antiemetic, antidiarrhoeal, immuno-stimulatory and antimicrobial activities. See Ahman, B., et al, "A Review on Pharmacological Properties of Zingerone (4-(4-Hydroxy-3-methoxyphenyl)-2-butanone)", Scientific World Journal. 2015; 2015: 816364. Zingerone is created by the heating or cooking of fresh ginger, which transforms gingerol to zingerone by a retroaldol reaction. Zingerone is present in ginger an amount of about 9.25%, and can be synthesized by, inter alia, the process disclosed in U.S. Pat. No. 2,381,210 to Cotton.

In some embodiments, the zingerone is present in an amount of from 0.01% to 1% (e.g., 0.05% to 0.5%; e.g., 0.05% to 0.350/%; e.g., 0.1%, 0.2%, or 0.3%) by weight of the composition.

Bisabolol

Bisabolol, (α-(−)-bisabolol, also known as levomenol), is a natural monocyclic sesquiterpene alcohol. It the primary constituent of the essential oil from German chamomile (*Matricaria recutita*) and *Myoporum crassifolium*. It has the formula:

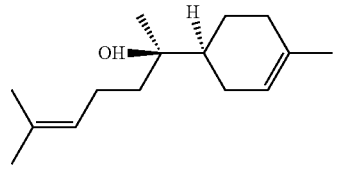 [SMILES: CC(C)=CCC[C@@](C)(O)[C@@H]1CC=C(C)CC1]

The (+) enantiomer, α-(+)-bisabolol, is also found naturally. As used herein, unless otherwise indicated, the term bisabolol includes both natural and synthetic bisabolol, and each isomer, and the racemic mixture α-(±)-bisabolol. In some embodiments, the bisabolol is present in the present compositions in an amount of from 0.01% to 1% (e.g., 0.05% to 0.5%; e.g., 0.05% to 0.35%; e.g., 0.1%, 0.2%, or 0.3%) by weight of the composition.

Zinc Salts

The compositions of the present disclosure contain zinc oxide and zinc citrate, preferably in a ratio of zinc oxide (wt. %) to zinc citrate (wt %) of from 1.5:1 to 4.5:1, e.g., 2:1, 2.5:1, 3:1, 3.5:1, or 4:1. Although the zinc citrate can be used in the present compositions in any hydrated or anhydrous form, the wt. percentages used herein refer to the trihydrate; i.e., zinc citrate trihydrate. In some embodiments, the zinc citrate is present in an amount of from 0.25 to 1.0 wt % (e.g., 0.5 wt. %) and zinc oxide is present in an amount of from 0.75 to 1.25 wt % (e.g., 1.0 wt. %) based on the weight of the oral care composition.

Stannous Ion Source

The oral care compositions may further include one or more stannous ion sources e.g. stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or a mixture thereof. In some preferred embodiments, the fluoride source is stannous fluoride. In some embodiments, the stannous fluoride is present in an amount of 0.1 wt. % to 2 wt. %, e.g. 0.1 wt %-0.6 wt. %, e.g., 0.4-0.5 wt. % of the total composition weight.

Abrasives

The compositions of the disclosure can include abrasives. Examples of suitable abrasives include silica abrasives, such as standard cleaning silicas, high cleaning silicas or any other suitable abrasive silicas. Additional examples of abrasives that can be used in addition to or in place of the silica abrasives include abrasives such as sodium metaphosphate, potassium metaphosphate, aluminum silicate, calcined alumina, bentonite or other siliceous materials, or combinations thereof.

Silica abrasive polishing materials useful herein, as well as the other abrasives, generally have an average particle size ranging between 0.1 and 30 microns, such as between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, the disclosures of which are incorporated herein by reference in their entireties. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, the disclosure of which is incorporated herein by reference in its entirety. In certain embodiments, abrasive materials useful in the practice of the oral care compositions in accordance with the disclosure include silica gels and precipitated amorphous silica having an oil absorption value of less than 100 cc/100 g silica, such as from 45 cc/100 g to 70 cc/100 g silica. Oil absorption values are measured using the ASTA Rub-Out Method D281. In certain embodiments, the silicas are colloidal particles having an average particle size of from 3 microns to 12 microns, and from 5 to 10 microns. Examples of low oil absorption silica abrasives useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from 7 to 10 microns in diameter, and an oil absorption of less than 70 cc/100 g of silica is an example of a low oil absorption silica abrasive useful in the practice of the present disclosure.

Any suitable amount of silica abrasive can be employed. In some embodiments, the present compositions include a synthetic amorphous precipitated abrasive silica in an amount of, e.g., 1%-25% by wt., e.g., 8%-25% by wt., e.g., 10%-15% by wt. In some embodiment, the present compositions further include a high cleaning silica, in an amount of, e.g., 1%-15% by wt., e.g., 5%-10%, e.g., 7% by wt.

Alkali Phosphate Salts

In some embodiments, the present compositions can include an effective amount of one or more alkali phosphate salts, e.g., sodium, or potassium salts, e.g., selected from alkali dibasic phosphate and alkali pyrophosphate salts. Suitable alkali phosphate salts include those selected from sodium phosphate dibasic, potassium phosphate dibasic, tetrasodium pyrophosphate, tetrapotassium pyrophosphate, sodium tripolyphosphate, disodium hydrogenorthophosphate, monosodium phosphate, pentapotassium triphosphate and mixtures of any of two or more of these, e.g., in an amount of 1-20%, e.g., 2-8%, e.g., 2-5%, by weight of the composition. In some embodiments, the polyphosphate is sodium tripolyphosphate, in an amount of from 1-5 wt %, e.g., about 3 wt %.

Polymers

The oral care compositions of the present disclosure also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include PVM/MA copolymers. The term "PVM/MA copolymer" as used herein is intended to include copolymers of maleic anhydride or acid with another polymerizable ethylenically unsaturated monomer, preferably methyl vinyl ether/maleic anhydride. In some embodiments, the copolymers include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation. In some embodiments, the present compositions include a PVM/MA copolymer, in an amount of from 0.1-5%, e.g., 0.2-2%, e.g., 0.3-1%, e.g., Gantrez S-97.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2-methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

Thickeners

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as xanthan gum, karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used. In some embodiments, the present compositions include carboxymethyl cellulose in an amount of from 0.1 wt. %-1.5 wt. %.

Surfactants

The present compositions can include one or more surfactants, for example anionic surfactants and zwitterionic (amphoteric) surfactants. Examples of suitable anionic surfactants include, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant. e.g., $C_6$-30 alkyl. In particular embodiments, the anionic surfactant is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%-2%, and optimal concentrations depend on the particular formulation and the particular surfactant. In one embodiment, the anionic surfactant is present at from 0.03% to 5% by weight, e.g., 1%-1%, e.g. 1.5%-2% by weight.

In some embodiments, the compositions of the present disclosure include an amphoteric surfactant. Suitable amphoteric surfactants include betaines and sultaines. In some embodiments, the amphoteric surfactant comprises a betaine having a quaternary ammonium or phosphonium ion as the cationic group and a carboxylate group as the anionic group; for example a betaine having a quaternary ammonium ion as the cationic group and a carboxylate group as the anionic group (i.e., a quaternary ammonium carboxylate betaine). Typical alkyldimethyl betaines include, but are not limited to, decyl dimethyl betaine or 2-(N-decyl-N, N-dimethylammonia)acetate, coco dimethyl betaine or 2-(N-coco N, N-dimethylammonia)acetate, myristyl dimethyl betaine, palmityl dimethyl betaine, lauryl dimethyl betaine, cetyl dimethyl betaine, stearyl dimethyl betaine, etc. The amidobetaines similarly include, but are not limited to, cocoamidoethylbetaine, cocoamidopropyl betaine and the like. In one embodiment, the betaine is cocamidopropyl betaine. Two examples of betaine surfactants that can be used are EMPIGEN™ BS/CA from Huntsman, and Tegobetaine F50 from BASF. Other suitable amphoteric surfactants include amine oxides.

In some embodiments, the compositions of the present disclosure comprise a single amphoteric surfactant. In some embodiments, the amphoteric surfactant is present in an amount of about 0.5 wt % to about 5 wt %, e.g. about 0.5 wt % to about 1.5 wt %, e.g. about 1 wt %.

In some embodiments, the surfactant system comprises a amphoteric surfactant and an anionic surfactant in a weight ratio of about 1:1 to about 1:3. In some embodiments, the ratio of amphoteric:anionic surfactant is about 1:1.5 to about 1:2, for example about 1:1.75.

Illustrative nonionic surfactants that can be used in the present compositions can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the present disclosure comprise a nonionic surfactant selected from poloxamers (e.g., poloxamer 407), polysorbates (e.g., polysorbate 20), polyoxyl hydrogenated castor oils (e.g., polyoxyl 40 hydrogenated castor oil), and mixtures thereof. When present, the nonionic surfactant can be present in an amount of from 0.1% to 3%, for example 0.1% to 1.5% by weight of the total composition.

Humectants

Within certain embodiments of the oral compositions, it is also desirable to incorporate one or more humectants to reduce evaporation and also contribute towards preservation by lowering water activity. Certain humectants can also impart desirable sweetness or flavor to the compositions. The humectant(s), on a pure humectant basis, are generally present in an amount of from 15% to 70% by weight, for example 30% to 65% by weight, for example 45-55% by weight of the composition.

Suitable humectants include edible polyhydric alcohols such as glycerine, sorbitol, xylitol, propylene glycol, polyethylene glycol, as well as other polyols and mixtures of these humectants. Mixtures of glycerine, propylene glycol and polyethylene glycol may be used in certain embodiments as the humectant component of the compositions herein. For example, in some embodiments, one or both of polyethylene glycol and propylene glycol is included, each in an amount of 1%-6% by weight.

Flavoring Agents

The present oral care compositions may also include a flavoring agent. Flavoring agents which are used in the present compositions include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The present oral care compositions also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present compositions are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %. The pyrophosphates also contribute to preservation of the compositions by lowering water activity.

Buffer

The present compositions can further include one or more buffering systems. One suitable buffering system is a mixture of citric acid and citrate ion, for example in a ratio of citric acid to citrate ion of from 1:3 to 1:10, e.g., 1:3 to 1:7, e.g. from 1:4 to 1:6, e.g. about 1:5, by weight, based on the weight of anhydrous citric acid and trisodium citrate dihydrate. Thus, in some embodiments, the present compositions include anhydrous citric acid in an amount of from 0.1-3 wt. %, e.g., 0.1-1 wt. %, e.g., 0.4-0.8 wt. %, e.g., about 0.6 wt. %; and trisodium citrate dihydrate, in an amount of from 0.1-5 wt. %, e.g., 2-4 wt. %, e.g., about 3 wt. %.

Water

Water is present in the oral compositions of the invention. Water, employed in the preparation of commercial oral compositions should be deionized and free of organic impurities. Water commonly makes up the balance of the compositions and includes from 5%-40%, e.g., 5%-25%, e.g., 5%-15%, e.g., about 8-10% by weight of the oral compositions. This amount of water includes the free water which is added, and does not include that amount which is introduced with other materials such as with sorbitol or silica or any components of the invention. The Karl Fischer method is a one measure of calculating free water.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

The present invention in its method aspect involves applying to the oral cavity a safe and effective amount of the compositions described herein.

The present compositions and methods (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLE 1

Dentifrice Formulations

The following dentifrice formulations were prepared:

Formula A: Stannous fluoride, zinc oxide, zinc citrate, 0.1% Zingerone

Formula B: Stannous fluoride, zinc oxide, zinc citrate, 0.1% Zingerone, 0.3% Bisabolol Formula C: Stannous fluoride, zinc oxide, zinc citrate, 0.3% Bisabolol Formula D: Stannous fluoride, zinc oxide, zinc citrate, 0.3% Zingerone Formula E: Stannous fluoride, zinc oxide, zinc citrate The compositions are shown in Table 1 below

TABLE 1

| Description | Formula A (wt %) | Formula B (wt %) | Formula C (wt %) | Formula D (wt %) | Formula E (wt %) |
| --- | --- | --- | --- | --- | --- |
| DEMINERALIZED WATER | 8.8 | 8.8 | 8.8 | 8.8 | 8.8 |
| SWEETENER | 0.80 | 0.80 | 0.80 | 0.80 | 0.80 |
| TRISODIUM CITRATE DIHYDRATE | 3.00 | 3.00 | 3.00 | 3.00 | 3.00 |

TABLE 1-continued

| Description | Formula A (wt %) | Formula B (wt %) | Formula C (wt %) | Formula D (wt %) | Formula E (wt %) |
|---|---|---|---|---|---|
| CITRIC ACID ANHYDROUS | 0.60 | 0.60 | 0.60 | 0.60 | 0.60 |
| STANNOUS FLUORIDE | 0.454 | 0.454 | 0.454 | 0.454 | 0.454 |
| ZINC OXIDE | 1.00 | 1.00 | 1.00 | 1.00 | 1.00 |
| ZINC CITRATE TRIHYDRATE | 0.50 | 0.50 | 0.50 | 0.50 | 0.50 |
| PHOSPHORIC ACID (85%) | 0.60 | 0.60 | 0.60 | 0.60 | 0.60 |
| SODIUM TRIPOLYPHOSPHATE | 3.00 | 3.00 | 3.00 | 3.00 | 3.00 |
| 99.0-101.0% GLYCERIN | 40.9 | 40.9 | 40.9 | 40.9 | 40.9 |
| POLYETHYLENE GLYCOL | 3.00 | 3.00 | 3.00 | 3.00 | 3.00 |
| PROPYLENE GLYCOL | 4.00 | 4.00 | 4.00 | 4.00 | 4.00 |
| PVP | 1.25 | 1.25 | 1.25 | 1.25 | 1.25 |
| DYE | 0.0019 | 0.0019 | 0.0019 | 0.0019 | 0.002 |
| TITANIUM DIOXIDE COATED MICA | 0.15 | 0.15 | 0.15 | 0.15 | 0.15 |
| THICKENERS (includes e.g., xanthan gum, carboxymentyl cellulose, microcrystalline cellulose/NaCMC) | 1.4 | 1.4 | 1.4 | v | 1.4 |
| ABRASIVES (includes, e.g., syn. amorph. ppt. silica, high cleaning silica, silicon dioxide) - ABRASIVE | 24.0 | 24.0 | 24.0 | 24.0 | 24.0 |
| ANIONIC SURFACTANT | 1.75 | 1.75 | 1.75 | 1.75 | 1.75 |
| AMPHOERIC SURFACTANT | 1.00 | 1.00 | 100 | 1.00 | 1.00 |
| PVM/MA COPOLYMER | 0.606 | 0.606 | 0.606 | 0.606 | 0.606 |
| SODIUM PHOSPHATE, TRIBASIC | 1.00 | 1.00 | 1.00 | 1.00 | 1.00 |
| FLAVOR | 2.10 | 1.80 | 1.90 | 1.90 | 2.20 |
| ZINGERONE (SYNTHETIC) | 0.10 | 0.10 | — | 0.30 | — |
| BISABOLOL (SYNTHETIC) | — | 0.30 | 0.30 | — | — |

EXAMPLE 2

Sn and Zn Deposition on Soft Tissue

Formulas A-E from Example 1 were tested as treatment on the gingival tissue (Mattek Corporation, Ashland Mass., GIN 606 or GIN 100). Oral-Gingival tissue was used. Slurry of the toothpaste was made in water 1:2 (1 part toothpaste to 2 parts water) and then 100 ul of slurry was applied on to each GIN 100 tissue sample. The slurry was let sit on tissue for 2 minutes. Each treatment was conducted on three replicate tissues. After 2 min treatment, the slurry was rinsed away with 200 ul of water with three washes. Tissues were then incubated overnight in media at 37° C. Replicate tissues from the same treatment were collected and digested with 0.5 ml of mixture of HCl and $HNO_3$ overnight at room temperature. Digested samples were diluted to 5 ml by adding distilled water. The samples were then centrifuged and supernatants were submitted for Sn and Zn quantification analysis by using ICP (ICP Atomic Emission Spectroscopy (ICP-AES Analysis).

The formulas that contain stannous fluoride with zinc oxide/zinc citrate and Zingerone (zingerone at either 0.1% or 0.3%; Formulas A and D) were not observed to affect the Sn and Zn deposition on human gingival tissue (versus Control Formula E). The formula that contains stannous fluoride with zinc oxide/zinc citrate and 0.3% of bisabolol (Formula C) slightly decreases both Sn and Zn deposition on human gingival tissue. However, the formula that contains stannous fluoride, zinc oxide/zinc citrate with both zingerone and bisabolol (Formula B) increases the Sn deposition specifically on human gingival tissue. The results are shown in Table 2 below:

TABLE 2

| Sn Deposition | |
|---|---|
| Formula | Sn Level (ppm) |
| A | 0.24 |
| B | 0.56 |
| C | 0.16 |
| D | 0.24 |
| E | 0.23 |

This phenomenon is also observed in a formulation similar to Formula B, but containing bisabolol at 0.2%. Measurement of Zn deposition of the Formulas A-E showed that Zn deposition was not significantly affected by the presence of zingerone, bisabolol, or both, demonstrating that this synergistic effect of zingerone and bisabolol is specific to Sn. The results are shown in Table 3:

TABLE 3

| Zn Deposition | |
|---|---|
| Formula | Zn Level (ppm) |
| A | 1.53 |
| B | 1.32 |
| C | 1.18 |
| D | 1.47 |
| E | 1.32 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:

1. An oral care composition comprising:
   a. from 0.01% to 1% bisabolol, based on the total weight of the composition;
   b. zinc oxide present in an amount of from 0.75 to 1.25 wt % and zinc citrate present in an amount of from 0.25 to 1.0 wt % based on the total weight of the composition;
   c. from 0.01% to 1 zingerone, based on the total weight of the composition; and
   d. a source of stannous ions, wherein the source of stannous ions is stannous fluoride in an amount of 0.1 wt. % to 2 wt. % based on the total weight of the composition.

2. The oral care composition of claim 1, wherein the zinc citrate is present in an amount of about 0.5 wt % and zinc oxide is present in an amount of about 1.0% based on the total weight of the composition.

3. The oral care composition of claim 1 further comprising synthetic amorphous precipitated abrasive silica in an amount of from 1%-25% by wt., based on the total weight of the composition.

4. The oral care composition of claim 1 further comprising:
   a high cleaning silica in an amount of from 1%-15% by wt. based on the total weight of the composition; and/or
   an effective amount of one or more alkali phosphate salts in an amount of from 1-5 wt %, based on the total weight of the composition.

5. The oral care composition of claim 1 further comprising:
   citric acid and tribasic citrate ion in an amount of from 0.1-3 wt. %, and citrate ion, in an amount of from 0.1-5 wt. %, based on the total weight of the composition; and/or
   carboxymethyl cellulose in an amount of from 0.1 wt. %, based on the total weight of the composition.

6. The oral care composition of claim 1 further comprising:
   an anionic surfactant, in an amount of from 0.5-5 wt. %, based on the total weight of the composition; and/or
   an amphoteric surfactant, in an amount of from 0.5-5% wt %, based on the total weight of the composition.

7. The oral care composition of claim 1, further comprising a PVM/MA copolymer, in an amount of from 0.1-5 wt. %, based on the total weight of the composition.

8. The oral care composition of claim 1, further comprising microcrystalline cellulose/sodium carboxymethylcellulose in an amount of from 0.1-5 wt. %, based on the total weight of the composition.

9. The oral care composition of claim 1, further comprising one or both of polyethylene glycol in an amount of from 1-6%; and propylene glycol in an amount of from 1-6%, based on the total weight of the composition.

10. The oral care composition claim 1, further comprising:
    polyvinylpyrrolidone (PVP) in an amount of from 0.5-3 wt. %, based on the total weight of the composition; and/or
    high cleaning silica in an amount of from 5%-10% wt. %, based on the total weight of the composition.

11. The oral care composition of claim 1, further comprising from 5%-40% free water by weight, based on the total weight of the composition.

12. The oral care composition of claim 1, further comprising one or more thickening agents.

13. The oral care composition of claim 1, comprising:
    i. about 0.1-0.3% bisabolol;
    ii. about 0.1-0.3% zingerone;
    iii. about 1.0% zinc oxide;
    iv. about 0.5% zinc citrate; and
    v. about 0.4%-0.5% stannous fluoride.

14. The oral care composition of claim 1, comprising:
    i. about 0.1-0.3% bisabolol;
    ii. about 0.1-0.3% zingerone;
    iii. about 1.0% zinc oxide;
    iv. about 0.5% zinc citrate;
    v. about 0.4%-0.5% stannous fluoride; and
    vi. about 12% abrasive silica.

15. The oral care composition of claim 1, wherein the oral composition may be any of the following oral compositions selected from the group consisting of: a toothpaste or a dentifrice, a mouthwash or a mouth rinse, a topical oral gel, a chewing gum, and a denture cleanser.

16. The oral care composition of claim 1, wherein the composition is obtained or obtainable by combining the ingredients as set forth in any of the preceding compositions.

17. A method to improve oral health comprising applying an effective amount of the oral composition of claim 1 to the oral cavity of a subject in need thereof, wherein the method is effective to:
    i. reduce or inhibit formation of dental caries,
    ii. reduce, repair or inhibit early enamel lesions, as detected by quantitative light-induced fluorescence (QLF) or electrical caries measurement (ECM),
    iii. reduce or inhibit demineralization and promote remineralization of the teeth,
    iv. reduce hypersensitivity of the teeth,
    v. reduce or inhibit gingivitis,
    vi. promote healing of sores or cuts in the mouth,
    vii. reduce levels of acid producing bacteria,
    viii. to increase relative levels of arginolytic bacteria,
    ix. inhibit microbial bio film formation in the oral cavity,
    x. raise and/or maintain plaque pH at levels of at least pH 5.5 following sugar challenge,
    xi. reduce plaque accumulation, xii. treat dry mouth,
xiii. enhance systemic health, including cardiovascular health,
xiv. Whiten teeth,
xv. reduce erosion of the teeth,
xvi. immunize (or protect) the teeth against cariogenic bacteria and their effects, and/or
xvii. clean the teeth and oral cavity.

* * * * *